US009965658B2

(12) United States Patent
Debates et al.

(10) Patent No.: US 9,965,658 B2
(45) Date of Patent: May 8, 2018

(54) PERSON-CENTRIC ACTIVATION OF RADIO FREQUENCY IDENTIFICATION (RFID) TAG

(71) Applicant: Motorola Mobility LLC, Chicago, IL (US)

(72) Inventors: Scott Debates, Crystal Lake, IL (US); Francis Forest, Chicago, IL (US); Douglas A. Lautner, Round Lake, IL (US)

(73) Assignee: MOTOROLA MOBILITY LLC, Chicago, IL (US)

( * ) Notice: Subject to any disclaimer, the term of this patent is extended or adjusted under 35 U.S.C. 154(b) by 0 days. days.

(21) Appl. No.: 14/740,305

(22) Filed: Jun. 16, 2015

(65) Prior Publication Data

US 2016/0371517 A1    Dec. 22, 2016

(51) Int. Cl.
*H04Q 5/22*      (2006.01)
*G08B 1/08*      (2006.01)
(Continued)

(52) U.S. Cl.
CPC ........ *G06K 7/10198* (2013.01); *A61B 5/0008* (2013.01); *A61B 5/01* (2013.01);
(Continued)

(58) Field of Classification Search
CPC ............. G06K 19/07749; G06K 19/02; G06K 19/0717; G06K 19/0723; G06K 19/07345;
(Continued)

(56) References Cited

U.S. PATENT DOCUMENTS 4,885,571 A * 12/1989 Pauley ................. G06K 7/0008
                                                340/514
7,168,626 B2 * 1/2007 Lerch ............... G06K 19/07381
                                                235/380
(Continued)

FOREIGN PATENT DOCUMENTS

DE     102013217559    3/2015
GB          2407189    4/2005
(Continued)

OTHER PUBLICATIONS

"Combined Search and Examination Report", GB Application No. 1609909.5, dated Dec. 6, 2016, 10 pages.
(Continued)

*Primary Examiner* — Emily C Terrell

(57) ABSTRACT

In embodiments of person-centric RFID tag activation, an RFID tag is configured so as to be active or inactive based on proximity to a person. An RFID tag includes an integrated circuit (IC), an antenna coupled to the IC, and skin proximity activation circuitry. For example embodiments, the skin proximity activation circuitry is configured to establish an active state for the RFID tag if proximate to skin and an inactive state if not proximate to skin. For an example implementation, an RFID tag is placed in an operationally active state in which an interrogation signal is detectable by an IC if at least one skin contact point is touching skin. For another example implementation, an RFID tag is placed in a communicatively active state in which a received interrogation signal may trigger the sending of a response signal if a detected temperature comports with a human-appropriate range of temperatures.

20 Claims, 12 Drawing Sheets

(51) Int. Cl.
*G08B 13/14* (2006.01)
*G08B 23/00* (2006.01)
*G06K 7/10* (2006.01)
*G06K 19/073* (2006.01)
*G06K 19/07* (2006.01)
*A61B 5/00* (2006.01)
*A61B 5/01* (2006.01)

(52) U.S. Cl.
CPC ..... *G06K 7/10019* (2013.01); *G06K 19/0716* (2013.01); *G06K 19/07309* (2013.01); *G06K 19/07354* (2013.01)

(58) Field of Classification Search
CPC ....... G06K 19/07758; G06K 19/07767; G06K 2017/0045; G06K 2017/009; A61B 5/0002; A61B 90/98; A61B 2562/08; A61B 90/90; A61B 2560/0462; A61B 5/00; A61B 5/1112; A61B 5/0008; A61B 5/0028; A61B 5/02; A61B 5/1113; A61B 5/150793; A61B 5/681; A61B 5/74; G08B 21/0211; G08B 21/0286; G08B 25/10; G08B 29/046; Y10S 128/903
USPC .................. 340/10.3, 539.1, 539.11, 539.12
See application file for complete search history.

(56) References Cited

U.S. PATENT DOCUMENTS

| | | | |
|---|---|---|---|
| 7,187,692 B1 | 3/2007 | Ooya et al. | |
| 7,948,381 B2 * | 5/2011 | Lindsay | G06K 19/0717 340/539.11 |
| 2005/0237156 A1 | 10/2005 | Scherabon | |
| 2006/0283960 A1 | 12/2006 | Top | |
| 2006/0290496 A1 * | 12/2006 | Peeters | A61B 5/0002 340/572.1 |
| 2007/0152829 A1 | 7/2007 | Lindsay et al. | |
| 2008/0259577 A1 * | 10/2008 | Hu | A61B 5/0002 361/749 |
| 2010/0123581 A1 | 5/2010 | Hatfield et al. | |
| 2010/0194541 A1 | 8/2010 | Stevenson et al. | |
| 2011/0233281 A1 | 9/2011 | Howell | |
| 2012/0235815 A1 * | 9/2012 | Coveley | G06K 19/07749 340/545.6 |
| 2012/0241524 A1 | 9/2012 | Blot et al. | |
| 2012/0326837 A1 | 12/2012 | Ajay et al. | |
| 2013/0057392 A1 * | 3/2013 | Bullock | G06K 7/10029 340/10.5 |
| 2014/0085050 A1 * | 3/2014 | Luna | G07C 9/00087 340/5.82 |
| 2014/0319225 A1 | 10/2014 | Van Rens | |

FOREIGN PATENT DOCUMENTS

| | | |
|---|---|---|
| GB | 2430097 | 3/2007 |
| WO | WO-9113285 | 9/1991 |
| WO | WO-2009091796 | 7/2009 |

OTHER PUBLICATIONS

"Extended European Search Report", EP Application No. 16173349.8, dated Oct. 24, 2016, 7 pages.

"Foreign Office Action", GB Application No. 1609909.5, dated Oct. 2, 2017, 3 pages.

* cited by examiner

Grasping a disable tab that is attached to an RFID tag that includes an integrated circuit coupled to an antenna, the RFID tag being in an inactive state in which the integrated circuit is incapable of responding to a received interrogation signal if the disable tab is attached to the RFID tag
402

Detaching the disable tab from the RFID tag to establish an active state of the RFID tag in which the integrated circuit is capable of responding to a received interrogation signal
404

Detecting that a disable tag has been detached from an RFID tag that includes an integrated circuit and an antenna
502

Responsive to detection of the detachment of the disable tag from the RFID tag, starting a timer of the integrated circuit
504

Receiving via the antenna of the RFID tag an interrogation signal
506

Responsive to receipt of the interrogation signal, sending via the antenna of the RFID tag a parameter derived from a value of the timer
508

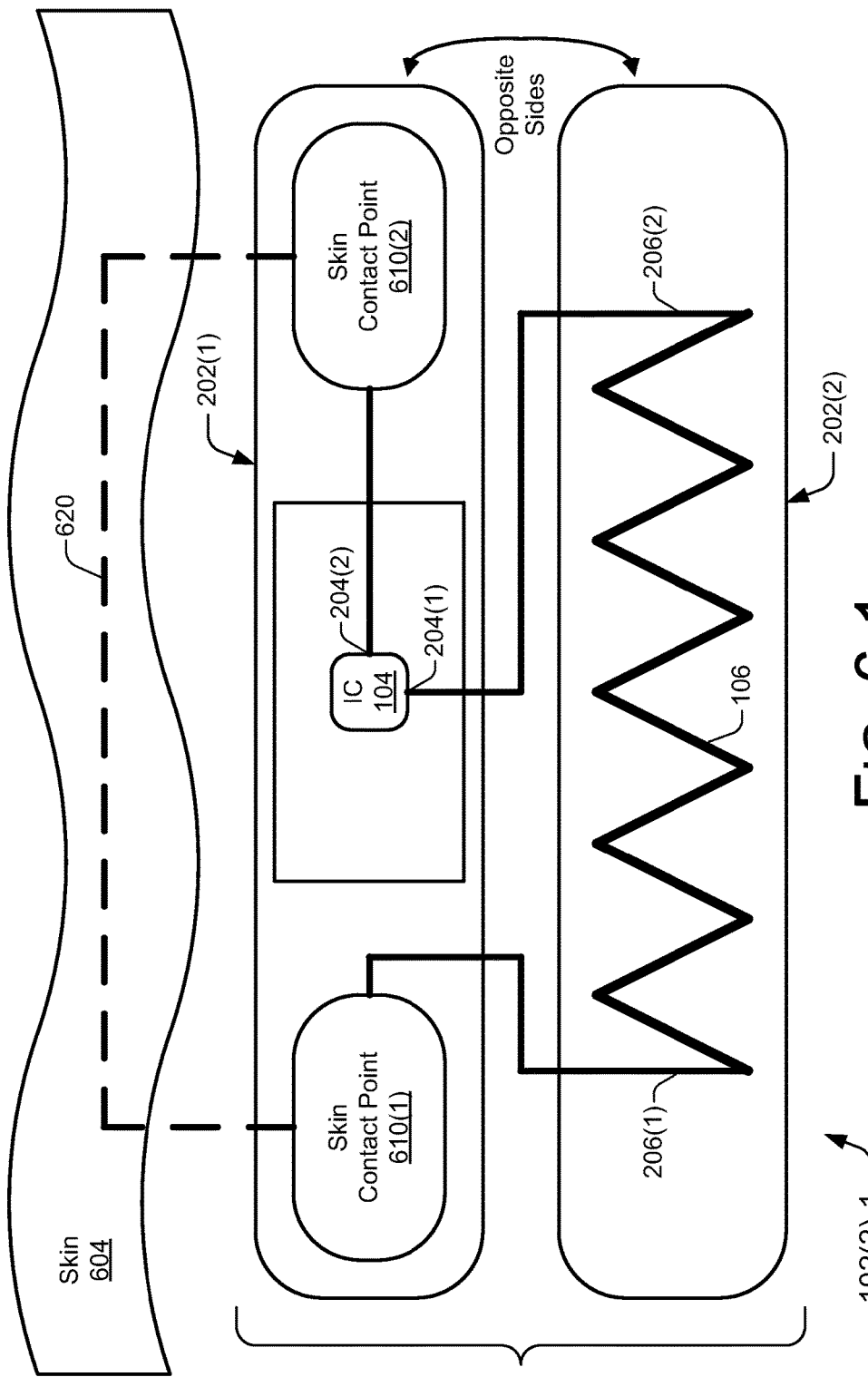

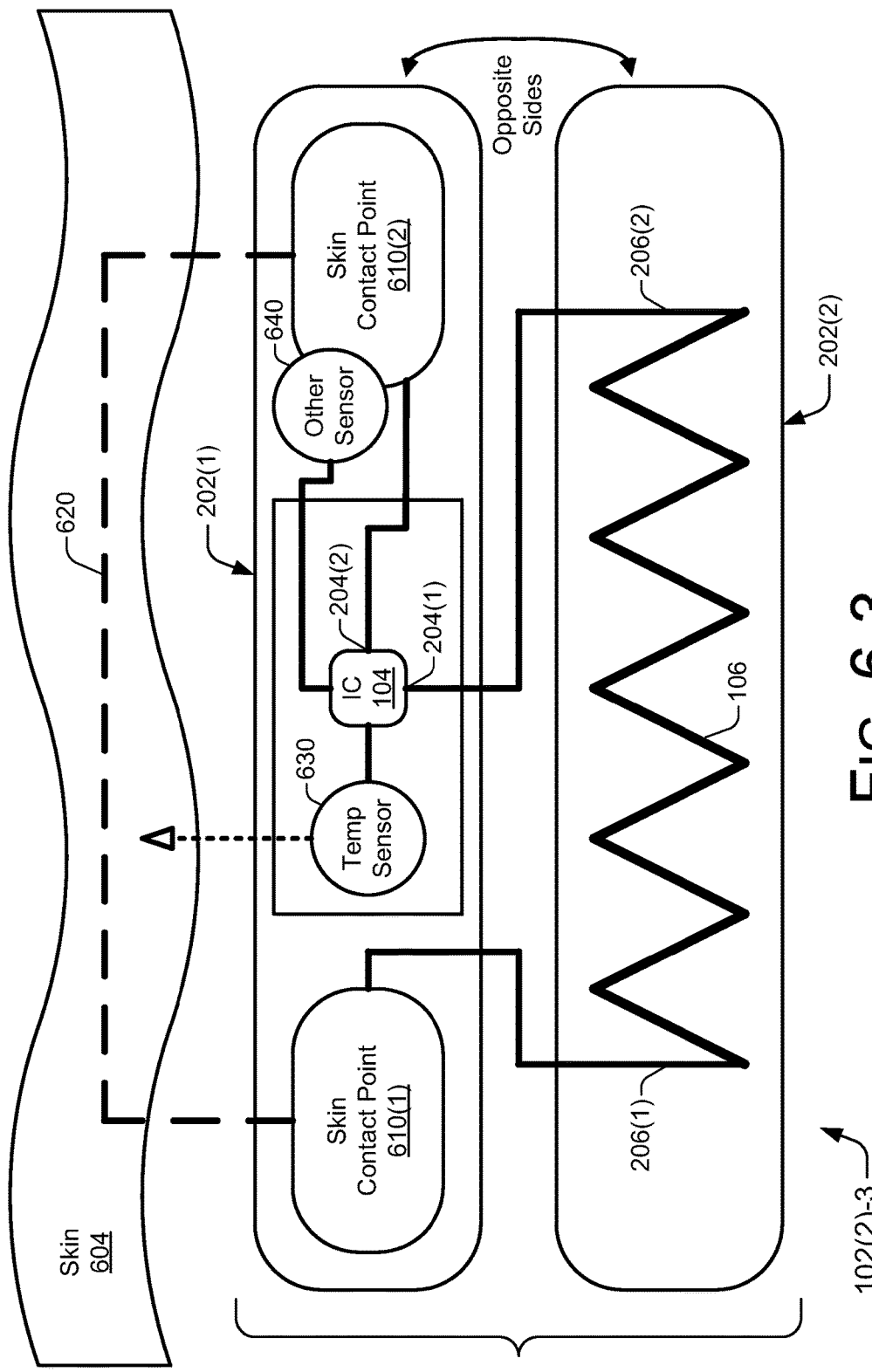

Remove at least one temporary cover to expose
a first skin contact point and a second skin contact point
of a medical implement comprising an RFID tag
including an integrated circuit and an antenna
702

Press the medical implement against a person to touch skin
at the first and second skin contact points to complete a circuit
including the antenna and to render the integrated circuit
capable of responding to an interrogation signal
704

Sensing a skin temperature to detect a temperature value
802

Comparing the detected temperature value
to at least one temperature threshold
804

Receiving an RFID interrogation signal
806

Determining whether to respond to the RFID
interrogation signal based on the comparing
808

PERSON-CENTRIC ACTIVATION OF RADIO FREQUENCY IDENTIFICATION (RFID) TAG

BACKGROUND

The acronym RFID is taken from the term "Radio-Frequency Identification." With RFID, small electronic tags are programmed with identifying data or other information. RFID tags are capable of wirelessly providing information using a radio frequency (RF) communication channel. In one example usage scenario, an inventory product code such as a stock-keeping unit (SKU) may be stored by an RFID tag to track inventory in a warehouse or to facilitate customer check-out in a store. RFID tags can therefore be used instead of bar codes. Bar codes are visual identifiers that necessitate line-of-sight to be acquired by a bar code reader. RFID tags, in contrast, do not require a line-of-sight view for RFID readers to acquire information that is stored on the RFID tags.

For responsive RFID tags, an RFID reader transmits an interrogation signal that effectively serves as a broadcast message requesting RFID tags that are in range to return information that the RFID tags have stored. If multiple RFID tags are in range, then an RFID reader may be inundated with multiple responses from multiple RFID tags. Multiple responses confuse the RFID reader such that at least some of the responses are not correctly received or not correctly interpreted. The more RFID tags that are in range of an interrogation signal that is transmitted by an RFID reader, the greater the likelihood that responses sent by the RFID tags will create mutual interference due to colliding signals and the larger the probability that the RFID reader will fail to correctly receive or will fail to correctly interpret all of the responses sent by the RFID tags.

As production costs have decreased, RFID tags have become more common. Cheaper RFID tags may become ubiquitous in the coming years for inventory purposes as well as for many other usage scenarios. Consequently, problems with reading RFID tags due to collisions of multiple responsive signals will become increasingly prevalent. The frequency of occurrence of tag reading collisions can be ameliorated, to some degree, using purely electronic approaches. However, such purely electronic approaches increase the cost and complexity of RFID readers or RFID tags, and purely electronic approaches may not be wholly effective or may not be universally applicable across different manufacturers or RFID platforms.

BRIEF DESCRIPTION OF THE DRAWINGS

Embodiments of on-demand activation of RFID tags and person-centric activation of RFID tags are described with reference to the following FIGS. The same numbers may be used throughout to reference like features or components that are shown in the FIGS.:

FIGS. 3-1, 3-2, and 3-3 are additional example RFID tags for implementations of on-demand RFID tag activation in accordance with one or more embodiments.

FIGS. 4 and 5 illustrate example methods for on-demand RFID tag activation in accordance with one or more embodiments.

FIGS. 6-1, 6-2, and 6-3 are additional example RFID tags for implementations of person-centric RFID tag activation in accordance with one or more embodiments.

FIGS. 7 and 8 illustrate example methods for person-centric RFID tag activation in accordance with one or more embodiments.

DETAILED DESCRIPTION

Figure 1:
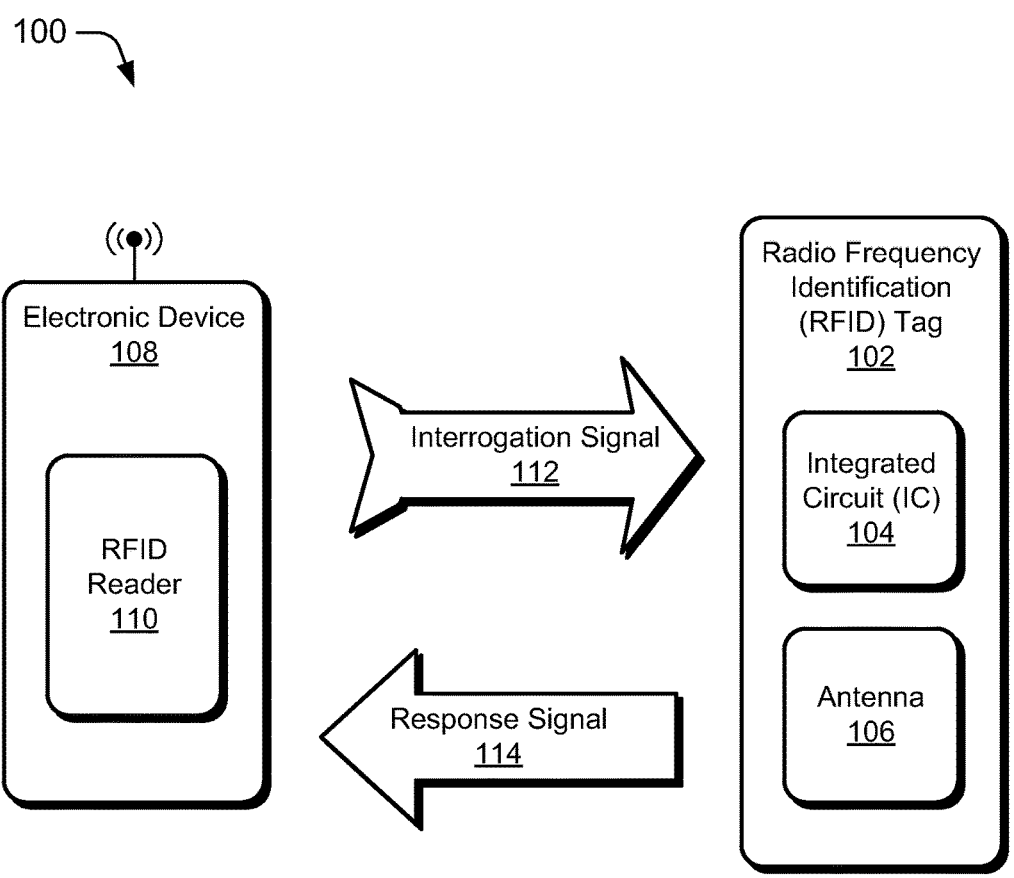
FIG. 1 illustrates an example RFID environment in which embodiments of on-demand RFID tag activation or person-centric RFID tag activation can be implemented.

RFID tags generally are capable of wirelessly providing information in response to an interrogation signal that is received from an RFID reader. If multiple RFID tags receive an interrogation signal transmitted from an RFID reader, then multiple RFID tags send back responses. The multiple responses can collide and confuse the RFID reader, which causes at least some of the responses to be unread or to be improperly interpreted. As noted above, there is some anti-tag collision technology that attempts to induce order on multiple RFID responses, but with the drawback that the technology adds complexity and cost to at least the RFID readers.

Another problem created from a proliferation of RFID tags is that RFID readers are more active receiving, demodulating, and interpreting responses from RFID tags, as well as any further processing of the information acquired from the received responses. These actions consume power, which is limited in battery-powered portable devices. If RFID tags are not usefully deployed but are susceptible to being read using an interrogation signal, the limited battery power of RFID readers may be consumed without fulfilling a useful purpose.

Yet another problem with existing RFID systems is that RFID tags are active upon their manufacture. Consequently, RFID tags may be responsively providing information that has no meaning or no real benefit. For example, an RFID tag that is to be used for inventory management may not yet be applied to an object, or an RFID tag that is to be used for tracking a package may be secured to a package that is not yet in transit. As another example, an RFID tag that is to facilitate safe consumption of a perishable food item may be created or may be secured to packaging of the food item prior to when the packaging is opened or prior to when the food item is removed from refrigeration. As still another example, a medical implement, such as a bandage or a sensor, that includes an RFID tag may provide RFID responses before the medical implement is placed on a person.

Embodiments of on-demand activation of RFID tags or person-centric activation of RFID tags can reduce the number of RFID tags in the field that are readable. Furthermore, embodiments can reduce the number of RFID tags that are active prior to being usefully deployed. Aspects described herein may include, for example, those that enable manual activation of an RFID tag by a user at a time of the user's choosing. Aspects described herein may further include, for example, those that enable automatic activation based on proximity to (e.g., contact with) the skin of a person.

For one or more embodiments, with regard to on-demand activation of RFID tags in particular, an RFID tag may be inactive until it is usefully deployed as determined by a person. For example, an RFID tag with a disable tab attached thereto may be incapable of responding to an interrogation signal until a person manually activates the RFID tag. An RFID tag may be activated by physically detaching the disable tab from the RFID tag. Detaching a disable tab may remove a short-circuit linkage that is coupled to an antenna lead of an RFID tag or that is coupled to an operability input of an integrated circuit of an RFID tag. Alternatively, an open circuit condition that is preventing functionality of an RFID tag may be eliminated by detaching a disable tab.

Upon activation, an RFID tag is enabled to respond to an interrogation signal, which is received from an RFID reader, with at least some information. A response signal from an RFID tag may include, for instance, an identification indication or an expiration date as at least part of the information. Alternatively, an RFID tag response may include a parameter derived from a sensor value obtained from a sensor that is on-board the RFID tag or a parameter derived from a time value (e.g., elapsed time) obtained from a timer that is on-board the RFID tag. Examples of sensor values include a temperature value representative of current or average temperature, a weight value representative of contents remaining in a package, and so forth.

For one or more embodiments, with regard to person-centric activation of RFID tags in particular, an RFID tag may be inactive until it is usefully deployed proximate to a person. For example, an RFID tag may have an open-circuit condition that is remedied by skin contact. A portion of the skin completes a circuit of the RFID tag and renders the RFID tag active so that the RFID tag is capable of responding to an interrogation signal. Alternatively, an RFID tag may include a temperature sensor that is adapted to measure a temperature of a person based on skin contact. If a sensed temperature is within a range indicative of a person, then an integrated circuit of the RFID tag responds to an interrogation signal; otherwise, the integrated circuit does not respond to a received interrogation signal.

Hence, upon activation based on skin proximity (e.g., skin contact), an RFID tag is configured to respond to an interrogation signal received from an RFID reader with at least some information. A response signal from an RFID tag may include, for instance, an identification of or a type of medication as at least part of the information. Alternatively, an RFID response may include a parameter derived from a sensor value obtained from a sensor that is on-board the RFID tag or a parameter derived from a time value (e.g., elapsed time) obtained from a timer that is on-board the RFID tag. Examples of sensor values include an electrical signal value representative of cardiac or brain activity, a temperature value representative of a patient's body temperature, a chemical indicator value representative of whether or a degree to which a particular chemical is detected, and so forth.

Embodiments of on-demand activation of RFID tags and person-centric activation of RFID tags are described herein below. General aspects are described with reference to FIGS. 1 and 2. Specific aspects of on-demand activation of RFID tags are described primarily, but not solely, with reference to FIGS. 3-5. Specific aspects of person-centric activation of RFID tags are described primarily, but not solely, with reference to FIGS. 6-8. However, aspects of on-demand activation of RFID tags and aspects of person-centric activation of RFID tags are described throughout the present disclosure. Moreover, although aspects of on-demand activation of RFID tags and aspects of person-centric activation of RFID tags are described somewhat separately, embodiments of on-demand activation of RFID tags and embodiments of person-centric activation of RFID tags may also be implemented jointly. By way of example only, an RFID tag may have a timer that is started by detaching a disable tab, and the RFID tag may be placed in an active state by being positioned against skin. As another example, activation of an RFID tag such that the RFID tag responds to interrogation signals may entail both detachment of a disable tab and detection of a temperature that is above a minimum body temperature or that is within a defined range of body temperatures.

Although features and concepts of on-demand RFID tag activation and person-centric RFID tag activation can be implemented in any number of different apparatuses, systems, environments, and/or configurations, embodiments of on-demand RFID tag activation and person-centric RFID tag activation are described in the context of the following example RFID tags, apparatuses, systems, and methods.

FIG. 1 illustrates an example RFID environment 100 in which embodiments of on-demand RFID tag activation or person-centric RFID tag activation can be implemented. RFID environment 100 is a logical or block diagram of an example RFID system. As illustrated, example RFID environment 100 includes a radio frequency identification (RFID) tag 102 having an integrated circuit (IC) 104 and an antenna 106, an electronic device 108 having an RFID reader 110, an interrogation signal 112, and a response signal 114. RFID reader 110 comprises at least a portion of electronic device 108. Examples of electronic devices 108 include an RFID reader gun, a mobile phone, a smart watch, a notebook computer, retail security scanning hardware, medical monitoring hardware, manufacturing or warehouse or retail inventory tracking hardware, a refrigerator, or some combination thereof.

For example embodiments, RFID reader 110 wirelessly transmits an interrogation signal 112 to one or more in-range RFID tags, such as RFID tag 102. RFID tag 102 receives interrogation signal 112, which effectively requests that RFID tag 102 provide information wirelessly. A request (not explicitly shown) of an interrogation signal 112 may specify particular information that is desired or may be asking for information generally. In response to receipt of the interrogation signal 112, IC 104 formulates response signal 114, and RFID tag 102 provides the response signal 114 wirelessly via antenna 106. RFID tag 102 may provide response signal 114 via a wireless communication that is sent over an air interface. A response signal 114 may be generated by RFID tag 102 as a version of a received interrogation signal 112 that comprises modulated RF backscatter off of antenna 106 of the RFID tag 102 or a reflected encoded version of the received interrogation signal 112. Additionally or alternatively, for a powered RFID tag 102, a response signal 114 may be transmitted using transmitter circuitry of the powered RFID tag 102.

RFID reader 110 receives wireless response signal 114 from RFID tag 102. Response signal 114 may include one or more pieces of information that RFID tag 102 is storing, has obtained, is producing, and so forth. Examples of information that can be included in a response signal 114 are an identification indication such as a code or an alphanumeric value, a parameter derived from a sensor including a sensor value, a parameter derived from a timer including a time value, a descriptive indication, or some combination thereof. Additional examples are described herein below.

RFID systems may be realized using at least low frequency (LF), high frequency (HF), or ultra-high frequency (UHF) radio waves. RFID systems may be passive or active. With active systems, RFID tags may include or otherwise have access to an independent power source, such as a battery. With passive systems, RFID tags harvest energy from an interrogation signal to enable the RFID tags to reflect back a response signal. Although not explicitly shown in the associated drawing figures, an RFID tag may include a capacitor or a small battery to temporarily collect and retain some of the energy harvested from an interrogation signal to power IC processing or sending of a response signal.

Alternative or hybrid RFID systems may also be implemented. Examples of other RFID systems include, but are not limited to, a passive reader active tag (PRAT) system that has a passive reader which receives radio signals from active tags (e.g., battery operated transmit only tags), an active reader passive tag (ARPT) system that has an active reader which transmits interrogation signals and also receives reply signals from passive tags, an active reader active tag (ARAT) system that uses active tags awoken or prompted by an interrogation signal sent from an active reader, a powered but passive tag system that has a powered passive tag (e.g., a battery-assisted passive (BAP) tag) that uses stored charge in a battery or capacitor to power continuous or repeated sensor reading and processing but awaits receipt of an interrogation signal before providing sensed values, or some combination thereof.

Figure 2:
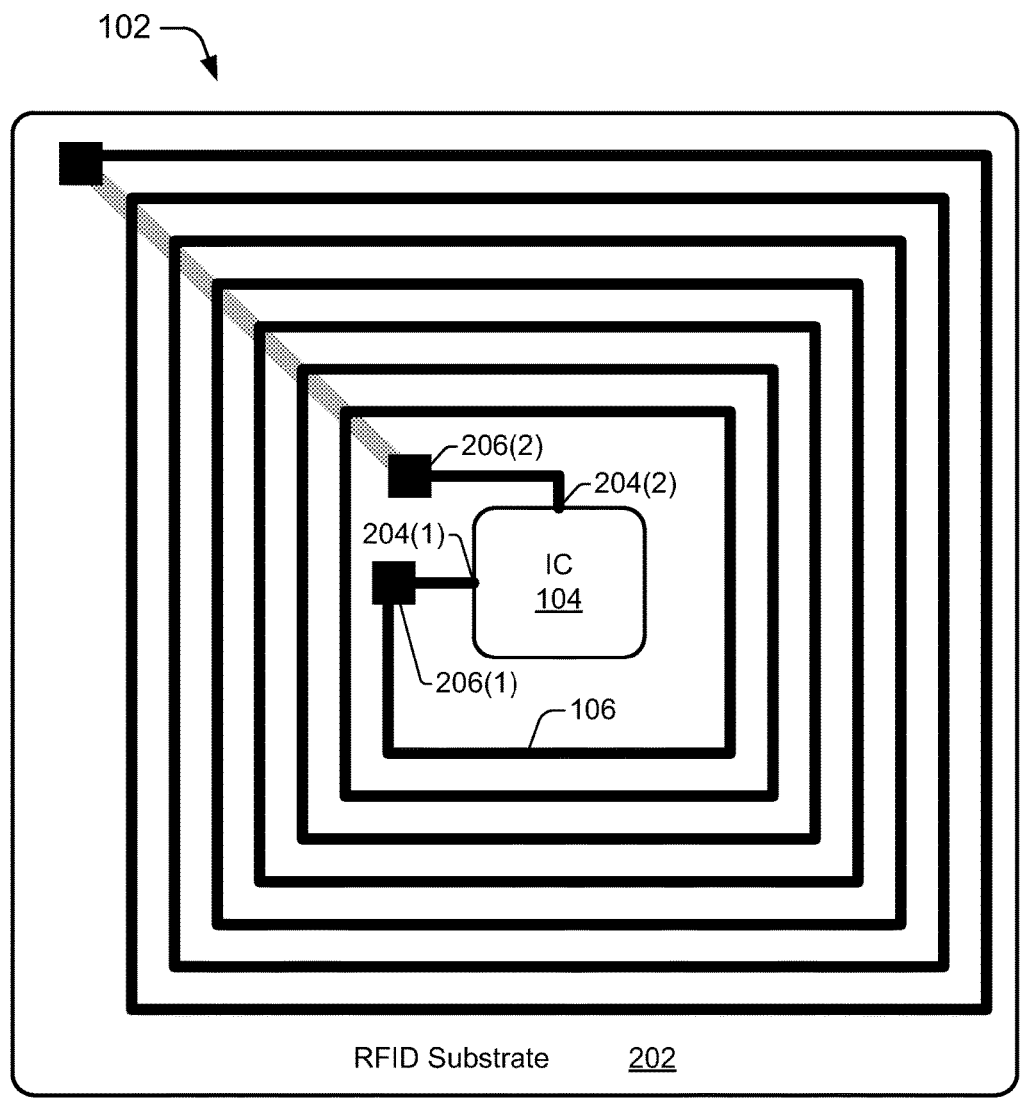
FIG. 2 illustrates an example RFID tag with which embodiments of on-demand RFID tag activation or person-centric RFID tag activation can be implemented.

FIG. 2 illustrates an example RFID tag 102 with which embodiments of on-demand RFID tag activation or person-centric RFID tag activation can be implemented. RFID tag 102 of FIG. 2 is a schematic diagram of an example RFID tag. For example embodiments, an RFID tag 102 may include an RFID substrate 202. Examples of an RFID substrate 202 are paper, plastic (e.g., flexible or rigid), wood, glass, ceramic, printed circuit board (PCB), or some combination thereof. An RFID substrate 202 may form a backbone or a foundation or a framework of a supporting structure for RFID tag 102. Alternatively, an RFID substrate 202 may be attached to, encapsulated within, incorporated as part of, etc. a backbone or a foundation or a framework of a supporting structure for RFID tag 102.

As illustrated in the example RFID tag 102 of FIG. 2, RFID substrate 202 includes or at least supports an IC 104 and an antenna 106. IC 104 includes two antenna terminals 204: a first antenna terminal 204(1) and a second antenna terminal 204(2). Antenna 106 includes two ends 206: a first antenna end 206(1) and a second antenna end 206(2). (The part of antenna 106 that is located at the top left corner of RFID substrate 202 may alternatively or additionally be considered second antenna end 206(2) (not explicitly indicated).) One of first antenna end 206(1) or second antenna end 206(2) may be considered an antenna loop in, and the other may be considered an antenna loop out. First antenna terminal 204(1) of IC 104 is coupled to first antenna end 206(1) of antenna 106, and second antenna terminal 204(2) of IC 104 is coupled to second antenna end 206(2) of antenna 106. Antenna 106 enables IC 104 to receive or send wireless signals for RFID tag 102.

IC 104 may be implemented using any of one or more processors (e.g., a microprocessor, a controller, a computing core, or a combination thereof) or processing systems with storage memory having processor-executable instructions that are fixed, hardware-encoded, programmable, alterable, wirelessly-receivable, or a combination thereof. IC 104 may be realized, by way of example but not limitation, as an application-specific integrated circuit (ASIC), a field-programmable gate array (FPGA), a complex programmable logic device (CPLD), an application-specific standard product (ASSP), a system on-a-chip (SoC), a silicon-based processing unit, or some combination thereof. Generally, an integrated circuit can be realized with hardware along with one or more of software, firmware, or fixed logic circuitry that is implemented in connection with processing or control circuits.

RFID tag 102 may further include processor-accessible storage memory (not explicitly shown) that is integrated with or discrete from IC 104. Storage memory enables persistent storage of data and processor-executable instructions (e.g., software applications, programs, functions, hard-coded operations, or a combination thereof). Storage memory can include various implementations of random access memory (RAM), read only memory (ROM), flash memory, or other types of storage media in various memory device configurations. Although not specifically indicated in FIG. 2, RFID tag 102 may further include an interconnect (e.g., a bus or other data transfer mechanism with traces, wires, buffers, etc.) that couples components of RFID tag 102 to each other. Although not depicted in FIG. 2, an RFID tag 102 may also include a power source, such as a single-use battery, a battery that is rechargeable by wire or wirelessly, a capacitor, a combination thereof, and so forth.

RFID tags may be produced in many different shapes, sizes, form factors, and materials. For example, RFID tags may be flat (i.e., two-dimensional) or three-dimensional (e.g., having an appreciable depth in addition to height and width). RFID tags may be square, rectangular, circular, triangular, box-shaped, spherical, cylindrical, and forth. Furthermore, RFID tags may be, for instance, at least as small as a grain of rice or at least as big as several inches across. An RFID substrate of an RFID tag may be adhered to another object, such as in a shipping or product label usage scenario; may be incorporated into another object, such as packaging material or a medical implement; may comprise an object having another purpose, such as for storage or shipping; and so forth. For example, an RFID substrate, or an IC and an associated antenna thereof, may form part of a cardboard shipping box or may be adhered to an underside of a milk container. Alternatively, an RFID substrate, or an IC and an associated antenna thereof, may comprise a bandage. Moreover, an RFID tag may be exposed or visible, or an RFID tag may be enclosed within or encapsulated by another material or object.

Figure 3:
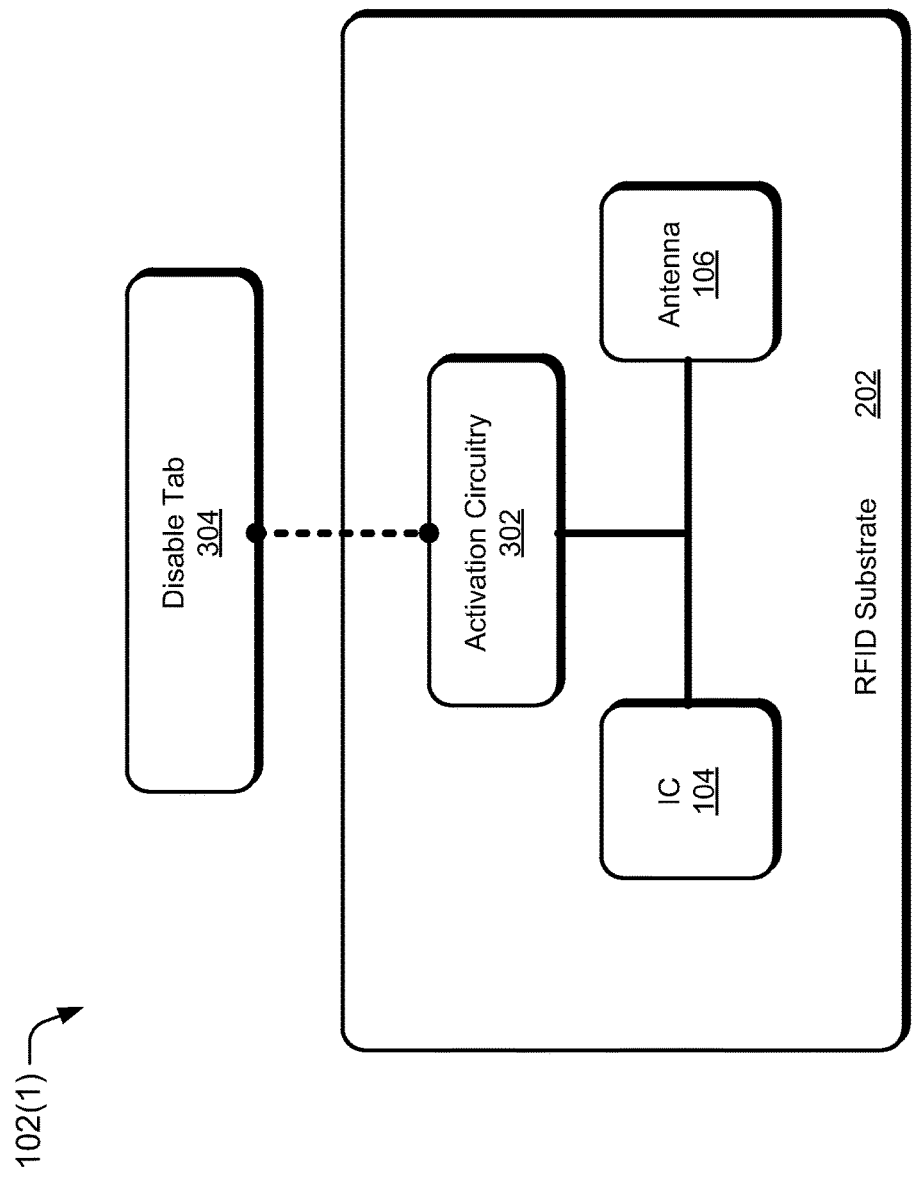
FIG. 3 illustrates an example RFID tag for implementations of on-demand RFID tag activation in accordance with one or more embodiments.
Figures 1, 3:
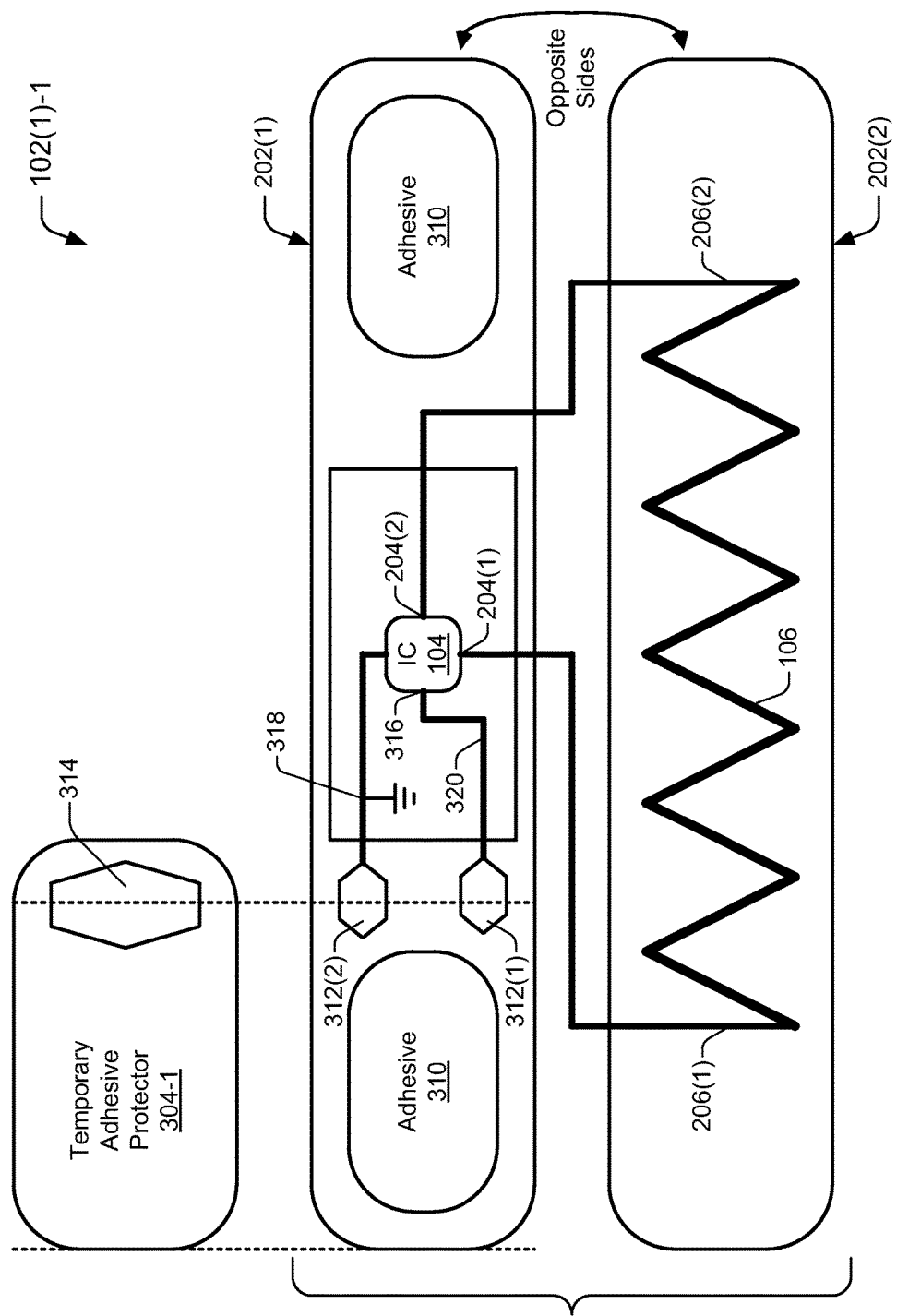
Figures 2, 3:
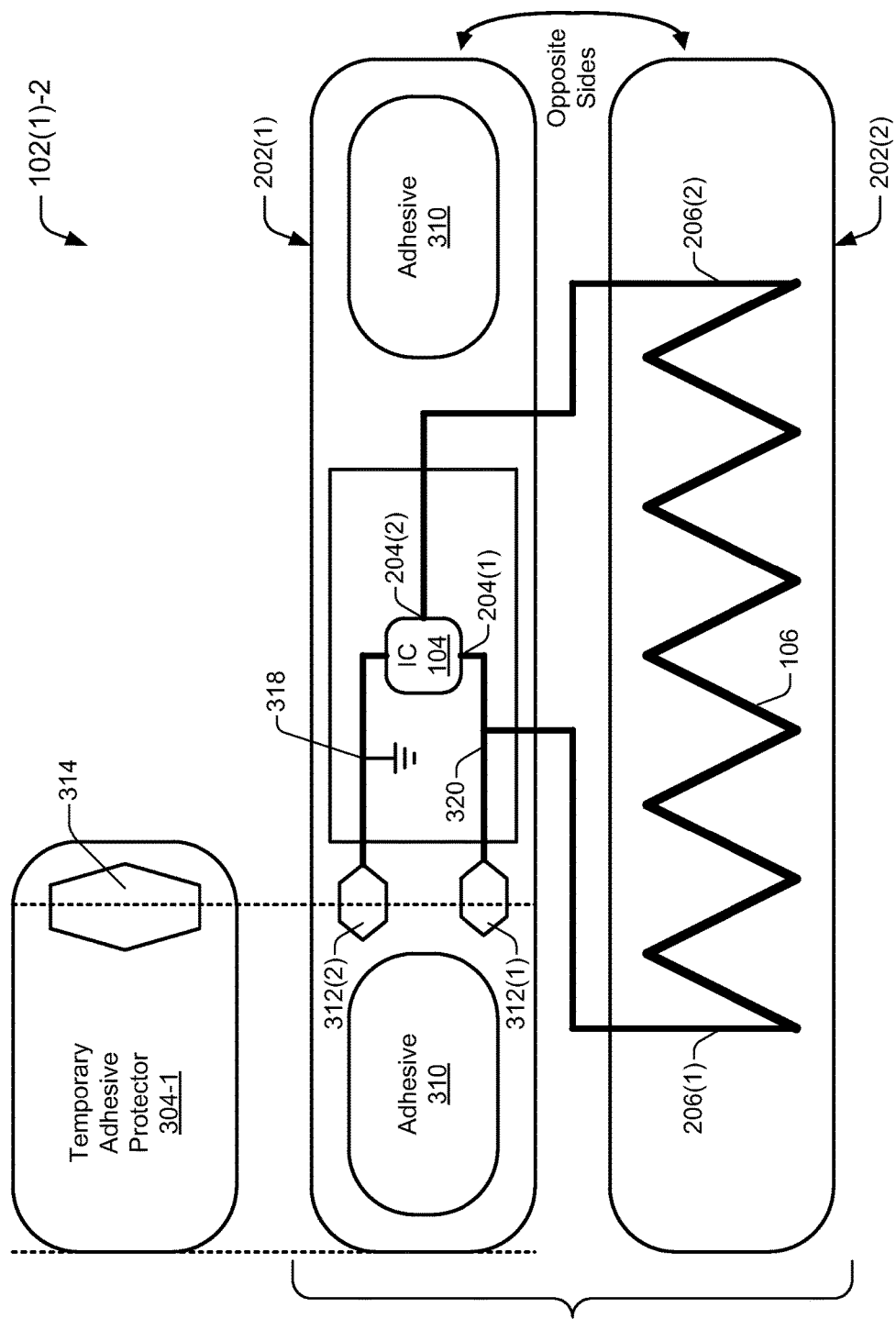
Figure 3:
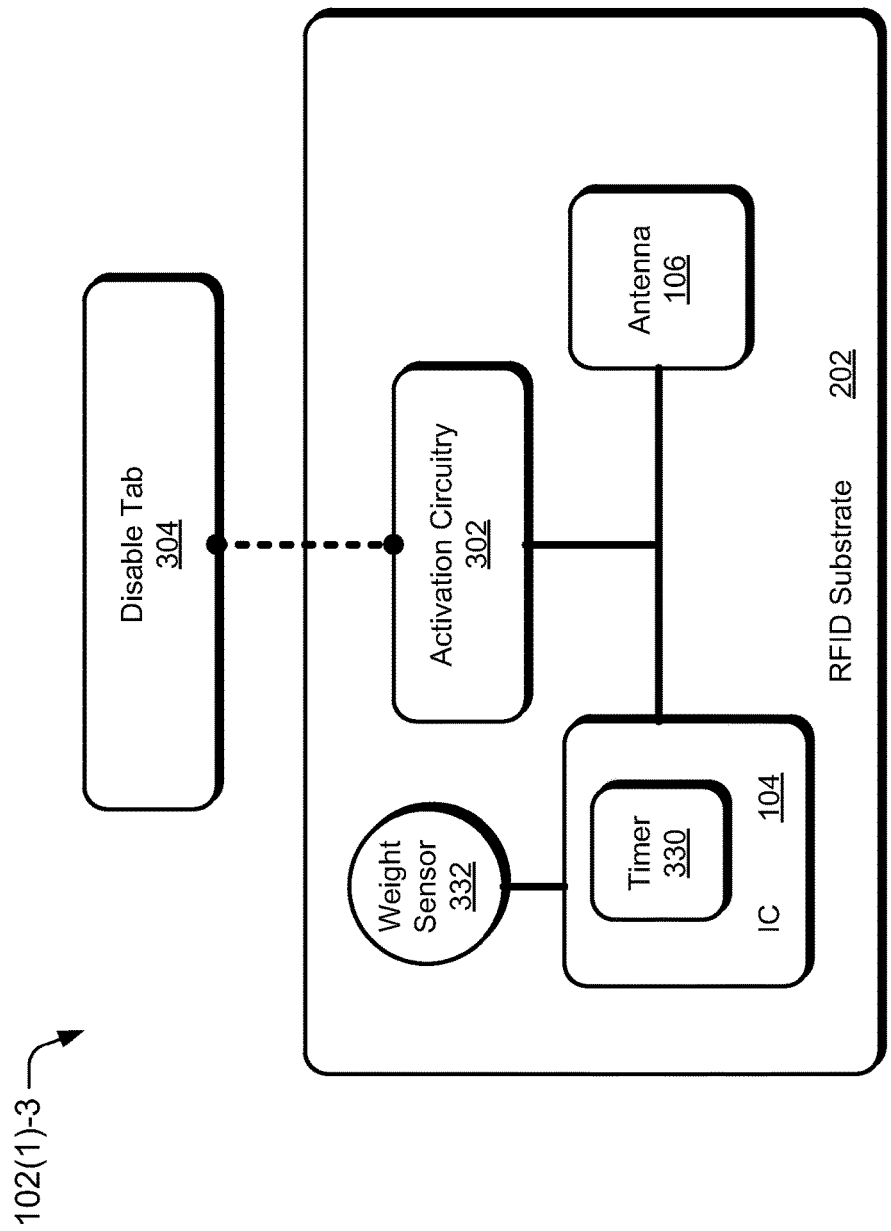

FIG. 3 illustrates an example RFID tag 102(1) for implementations of on-demand RFID tag activation in accordance with one or more embodiments. As illustrated in logical or block diagram form, example RFID tag 102(1) includes an RFID substrate 202, an IC 104, an antenna 106, activation circuitry 302, and a disable tab 304. IC 104 is coupled to antenna 106 or activation circuitry 302; antenna 106 is coupled to IC 104 or activation circuitry 302; and activation circuitry 302 is coupled to IC 104 or antenna 106. Disable tab 304 may be included as part of or may be separate from RFID substrate 202.

For example embodiments, disable tab 304 is detachably attached to RFID tag 102(1). RFID tag 102(1) is in an inactive state if disable tab 304 is attached, but RFID tag 102(1) is in an active state if disable tab 304 is detached from RFID tag 102(1). Activation circuitry 302, based at least partially on if disable tab 304 is attached to RFID tag 102(1), places RFID tag 102(1) in, or causes RFID tag 102(1) to be in, an active state or an inactive state. With an active state, RFID tag 102(1) is responsive to an interrogation signal. With an inactive state, RFID tag 102(1) is not responsive to an interrogation signal. In operation, RFID tag 102(1) may be manufactured to be in an inactive state due to the presence of disable tab 304. To activate RFID tag 102(1) on-demand, a person or end-user may detach disable tab 304. Detachment of disable tab 304 (e.g., separation, tearing, removal, etc. of disable tab 304 from RFID tag 102(1)) may be partial or may be complete. Detachment of disable tab 304 (e.g., dislocation, peeling back, withdrawal, etc. of disable tab 304 from RFID tag 102(1)) may be permanent or may be subject to re-attachment to deactivate RFID tag 102(1).

For one or more example embodiments, antenna 106 is configured to receive an interrogation signal (e.g., interrogation signal 112). IC 104 is coupled to antenna 106. IC 104 is capable of processing and responding to the interrogation signal if RFID tag 102(1) is in an active state, and IC 104 is incapable of responding to the interrogation signal if RFID tag 102(1) is in an inactive state. Disable tab 304 is detachable from RFID tag 102(1). Activation circuitry 302 is configured to establish the inactive state if disable tab 304 is attached to RFID tag 102(1) or to establish the active state if disable tab 304 is detached from RFID tag 102(1). Example implementations of activation circuitry 302 are described below with particular reference to FIGS. 3-1 and 3-2.

FIG. 3-1 depicts additional example RFID tag implementations for on-demand activation of RFID tags in accordance with one or more embodiments. As illustrated, RFID tag 102(1)-1 is a schematic diagram of an example RFID tag that is depicted as a medical implement. Specifically, RFID tag 102(1)-1 is shown as a bandage with centralized protective padding, which may include topical medicine, at least one sensor, and so forth. However, RFID tag 102(1)-1 may be realized as another type of medical implement, such as a medical sensor, a label, as an inventory tracking mechanism, some combination thereof, and so forth.

For example embodiments, RFID tag 102(1)-1 includes (i) an RFID substrate 202 (e.g., also of FIG. 2) having a first RFID substrate side 202(1) and a second RFID substrate side 202(2) and (ii) a detachably attached temporary adhesive protector 304-1. Opposite sides of the RFID substrate 202 are shown as first RFID substrate side 202(1) and second RFID substrate side 202(2). Certain components are shown on the respective RFID substrate sides to avoid visually obscuring relevant components or interrelationships of the components. Although certain components are shown with respect to a particular substrate side, one or more of the components may be on a same side, may be distributed across the two sides differently than is depicted, may be implemented fully or partially within the substrate, some combination thereof, and so forth.

Second RFID substrate side 202(2) includes an antenna 106 having a first antenna end 206(1) and a second antenna end 206(2). First RFID substrate side 202(1) includes an IC 104, at least one adhesive portion 310, at least one circuit element 312 that is part of activation circuitry 302 (e.g., of FIG. 3), a ground node 318, and a connective circuit element 320. IC 104 includes a first antenna terminal 204(1), a second antenna terminal 204(2), and an operability input 316, as well as a terminal to ground node 318. At least one circuit element 312 may include a first circuit element 312(1) and a second circuit element 312(2). As shown, first RFID substrate side 202(1) includes two adhesive portions 310, but more or fewer may be included on either or both of first and second RFID substrate sides 202(1) and 202(2).

Temporary adhesive protector 304-1 is an example implementation of a disable tab 304 (e.g., of FIG. 3). Temporary adhesive protector 304-1 includes at least one conductive element 314 and is adapted to cover adhesive 310, at least until a person wishes to adhere RFID tag 102(1)-1 to another object. Alternatively, a disable tab 304 may be attached to an RFID tag using a different mechanism than an adhesive, such as a perforated tear-able material, a break-away material, and so forth. A circuit element 312 may comprise, for example, a pad, a connective circuit element, a one or two-dimensional conductive element, an electrical contact, or some combination thereof. Operability input 316 may comprise, for example, a reset input, a chip enable input, a standby input, or some combination thereof. Connective circuit element 320 may comprise, for example, a conductive material connecting two or more other circuit elements, a trace, a lead line, a wire, a portion of a bus, or some combination thereof.

In example operative embodiments, first antenna end 206(1) is coupled to first antenna terminal 204(1) of IC 104, and second antenna end 206(2) is coupled to second antenna terminal 204(2) of IC 104. First circuit element 312(1) is coupled (e.g., via connective circuit element 320) to operability input 316 of IC 104. Second circuit element 312(2) is coupled to ground node 318. For an inactive state of RFID tag 102(1)-1 in which IC 104 is incapable of responding to an interrogation signal 112 (e.g., of FIG. 1), temporary adhesive protector 304-1 is flipped over and positioned (i) such that temporary adhesive protector 304-1 covers adhesive portion 310 (e.g., adhesive portion 310 on the left side of first RFID substrate side 202(1) of FIG. 3-1) and (ii) such that conductive element 314 contacts first circuit element 312(1) and second circuit element 312(2).

If temporary adhesive protector 304-1 is attached to RFID tag 102(1)-1, a short-circuit condition is established between first circuit element 312(1) and second circuit element 312(2) with a short-circuit linkage created by conductive element 314. This short-circuit condition couples operability input 316 of IC 104 to ground node 318, which disables IC 104 in this implementation. Even if an interrogation signal is received by RFID tag 102(1)-1 via antenna 106, IC 104 is incapable of responding to the interrogation signal. If a person is ready to activate RFID tag 102(1)-1, the person may detach temporary adhesive protector 304-1 from RFID tag 102(1)-1. This eliminates the short-circuit condition created by conductive element 314 between first circuit element 312(1) and second circuit element 312(2) by removing the short-circuit linkage. If operability input 316 of IC 104 is not forced to ground, IC 104 is capable of responding to an interrogation signal that is received via antenna 106 and RFID tag 102(1)-1 is in an active state.

The example RFID tag implementations for on-demand activation of RFID tags that are described above and illustrated in FIG. 3-1 establish an inactive state by instituting a short-circuit condition between an operability input 316 of IC 104 and a ground node 318. In contrast, example RFID tag implementations for on-demand activation of RFID tags that are described below and illustrated in FIG. 3-2 establish an inactive state by instituting a short-circuit condition between an antenna end 206 of antenna 106 and a ground node 318.

FIG. 3-2 depicts additional example RFID tag implementations for on-demand activation of RFID tags in accordance with one or more embodiments. For example embodiments, RFID tag 102(1)-2 includes (i) an RFID substrate 202 having a first RFID substrate side 202(1) and a second RFID substrate side 202(2) and (ii) a removable temporary adhesive protector 304-1. Second RFID substrate side 202(2) includes an antenna 106 having a first antenna end 206(1) and a second antenna end 206(2). First RFID substrate side 202(1) includes an IC 104, at least one adhesive portion 310, at least one circuit element 312 that is part of activation circuitry 302 (e.g., of FIG. 3), a ground node 318, and a connective circuit element 320. IC 104 includes a first antenna terminal 204(1) and a second antenna terminal 204(2), as well as a terminal to ground node 318. At least one circuit element 312 may include a first circuit element 312(1) and a second circuit element 312(2). Temporary adhesive protector 304-1 includes conductive element 314.

In example operative embodiments, first antenna end 206(1) is coupled to first antenna terminal 204(1) of IC 104, and second antenna end 206(2) is coupled to second antenna terminal 204(2) of IC 104. First circuit element 312(1) is a circuit element that is coupled (e.g., via connective circuit element 320) to first antenna terminal 204(1) of IC 104 and first antenna end 206(1). Second circuit element 312(2) is a grounded circuit element that is coupled to ground node 318. For an inactive state of RFID tag 102(1)-2 in which IC 104 is incapable of responding to an interrogation signal 112 (e.g., of FIG. 1), temporary adhesive protector 304-1 is flipped over and positioned (i) such that temporary adhesive protector 304-1 covers adhesive portion 310 (e.g., adhesive portion 310 on the left side of first RFID substrate side 202(1) of FIG. 3-1) and (ii) such that conductive element 314 contacts first circuit element 312(1) and second circuit element 312(2).

If temporary adhesive protector 304-1 is attached to RFID tag 102(1)-2, a short-circuit condition is established between first circuit element 312(1) and second circuit element 312(2) with a short-circuit linkage created by conductive element 314. This short-circuit condition couples first antenna end 206(1) (and first antenna terminal 204(1) of IC 104) to ground node 318. In this implementation, grounding antenna 106 effectively prevents receipt of an interrogation signal or effectively disables wireless energization of RFID tag 102(1)-2. Even if an interrogation signal arrives at RFID tag 102(1)-2 from an RFID reader, IC 104 is incapable of responding to the interrogation signal. If a person is ready to activate RFID tag 102(1)-2, the person may detach temporary adhesive protector 304-1 from RFID tag 102(1)-2. This eliminates the short-circuit condition created by conductive element 314 between first circuit element 312(1) and the grounded second circuit element 312(2) by removing the short-circuit linkage. If first antenna end 206(1), and first antenna terminal 204(1) of IC 104 that is coupled thereto, is not forced to ground, IC 104 is capable of responding to an interrogation signal that is received via antenna 106 and RFID tag 102(1)-2 is in an active state.

FIG. 3-3 depicts additional example RFID tag implementations for on-demand activation of RFID tags in accordance with one or more embodiments. As illustrated, RFID tag 102(1)-3 includes, like RFID tag 102(1) of FIG. 3, an RFID substrate 202, an IC 104, an antenna 106, activation circuitry 302, and a disable tab 304. RFID tag 102(1)-3 further includes a timer 330 and a weight sensor 332. For example embodiments, an RFID tag 102 may include a timer 330 or a weight sensor 332. Timer 330 is shown integrated with IC 104, and weight sensor 332 is shown being coupled thereto. However, the timer 330 or the weight sensor 332 may be integrated with or discrete from an IC 104.

For an example RFID tag 102(1)-3 implementation that includes a timer 330, the timer 330 may keep track of real-world clock time (or time and date) once programmed with a current time or date, may track elapsed time once started, may track countdown time once started, or a combination thereof. Time tracking, such as counting upward for elapsed time or downward toward an expiration time, may be started as part of a manufacturing process of RFID tag 102(1)-3, may be started in response to a received interrogation signal—which triggering signal may include an instruction or command to start a timer, may be started responsive to disable tab 304 being detached from RFID tag 102(1)-3, some combination thereof, and so forth.

Timer 330 may include a time value that affects if or how IC 104 may respond to an interrogation signal. In other words, an existence, a content, a timing, etc. of a response by an IC 104 may be based at least partially on a parameter that is derived from a time value of timer 330. Examples of a parameter include a current value of a timer, an alert that depends on a time value, an expiration indication, a difference between a current time value and a perishable period, or some combination thereof. For example, IC 104 may report a current time value in response to an interrogation signal, IC 104 may respond if a time value is changing (i.e., if a timer 330 has been started) but not otherwise, IC 104 may respond with an alert if a certain amount of time has transpired (e.g., if a countdown timer has expired or if a count-up timer reaches one or more or threshold levels), or some combination thereof.

For an example usage scenario, disable tab 304 of RFID tag 102(1)-3 may be de-attached if an item is opened or if a container is supplied with a perishable product. Afterwards, if a perishable period has expired, RFID tag 102(1)-3 may respond to an interrogation signal with a warning indication. If a perishable period has not transpired, RFID tag 102(1)-3 may respond with an "ok," may respond with an indication of a remaining safe time, or may elect to not respond to an interrogation signal. IC 104 may be manufactured with at least one value representative of a perishable period, or RFID tag 102(1)-3 may be programmed with a perishable period wirelessly.

For an example RFID tag 102(1)-3 implementation that includes a weight sensor 332, weight sensor 332 may measure/detect a weight of an object to which RFID tag 102(1)-3 is secured an output an indication of the detected weight. In other words, an existence, a content, a timing, etc. of a response by an IC 104 may be based at least partially on a parameter that is derived from a weight value. Examples of a parameter include a current value of a weight sensor, a notification that depends on a current weight value, a difference between a current weight value and an original or first weight value, an indication of time remaining until product weight becomes negligible—e.g. based on a rate of reduction of weight, or some combination thereof. IC 104 may be configured to track changes in the weight of an object over time or to at least provide a weight value representative of a current weight.

For an example usage scenario, in response to receiving an interrogation signal, RFID tag 102(1)-3 may be configured to send an indication of remaining product (e.g., cereal, milk, eggs, flour, pills, or liquid medicine) in a package with which it is associated, such as being incorporated into or adhered to the packaging. Example indications of remaining product may include values representative of ounces, percentage remaining or used, "full," one-quarter consumed, product not needed currently, more product needed, an integer quantity used or remaining, an expected time period until a remaining product is consumed based on a historical rate of consumption, or a combination thereof.

The example RFID tag implementations for on-demand activation of RFID tags that are described herein above and illustrated in FIGS. 3-1 and 3-2 establish an inactive state by instituting a short-circuit condition between a ground node and another node of RFID tags 102(1)-1 and 102(1)-2. Alternatively, a disable tab 304 may establish an inactive state by instituting an open-circuit condition in activation circuitry 302 of an RFID tag 102. For example, a disable tab 304 may include an insulating element having a non-conductive portion (e.g., made of plastic) that is disposed between two conductive contacts of activation circuitry 302 of an RFID substrate 202 to establish an inactive state of RFID tag 102. If disable tab 304 is detached from RFID tag 102, the two conductive contacts are permitted to touch (e.g., under a spring-like or tension mechanism) to complete a circuit that establishes an active state for RFID tag 102 to enable an IC 104 and an antenna 106 to receive and respond to an interrogation signal.

FIGS. 4 and 5 illustrate example methods for on-demand RFID tag activation in accordance with one or more embodiments. The order in which the methods are described is not intended to be construed as a limitation, and any number or combination of the described method operations can be performed in any order or with any amount of temporal overlap to perform a method, or an alternate method.

For flow diagram 400 of FIG. 4, operations 402-404 may be performed by a person. At block 402, a disable tab that is attached to an RFID tag that includes an integrated circuit coupled to an antenna is grasped, with the RFID tag being in an inactive state in which the integrated circuit is incapable of responding to a received interrogation signal if the disable tab is attached to the RFID tag. For example, a person may grasp a disable tab 304 that is attached to an RFID tag 102(1) that includes an IC 104 coupled to an antenna 106, with RFID tag 102(1) being in an inactive state in which IC 104 is incapable of responding to a received interrogation signal 112 if disable tab 304 is attached to (e.g., and providing a short-circuit current path to ground in activation circuitry of or instituting an open-circuit condition in activation circuitry of) RFID tag 102(1).

At block 404, the disable tab is detached from the RFID tag to establish an active state of the RFID tag in which the integrated circuit is capable of responding to a received interrogation signal. For example, a person may detach disable tab 304 from RFID tag 102(1) to (e.g., eliminate a short-circuit current condition between a circuit node and ground to thereby) establish an active state of RFID tag 102(1) in which IC 104 is capable of responding to a received interrogation signal 112 (e.g., by formulating and sending a response signal 114).

For flow diagram 500 of FIG. 5, operations 502-508 may be performed by an RFID tag 102. Methods or operations described herein can be implemented using hardware in conjunction with software, firmware, fixed logic circuitry, a combination thereof, and so forth. Some operations of the example methods may be described in a general context of processor-executable instructions that are stored on processor-accessible (e.g., computer-readable) storage memory that is part of an RFID tag 102 (e.g., that is disposed on an RFID substrate 202 as part of, or separate from, an IC 104).

At block 502, detachment of a disable tag from an RFID tag, which includes an integrated circuit and an antenna, is detected. For example, an RFID tag 102(1) may detect that a disable tab 304 is detached (e.g., partially or fully) from RFID tag 102(1) (e.g., because an open-circuit condition or a short-circuit condition that was preventing at least some of the functionality of the RFID tag—such as an ability to respond to an interrogation signal—is eliminated and wireless functionality is initiated), which RFID tag 102(1) includes an IC 104 and an antenna 106.

At block 504, responsive to detection of the detachment of the disable tag from the RFID tag, a timer of the integrated circuit is started. For example, if RFID tag 102(1) detects that disable tab 304 is detached therefrom, a timer 330 of IC 104 may be started (e.g., a time value may be incremented or decremented at a known rate). For instance, a timer 330 may start counting down from a time value that is initially set to coincide with a perishability period, such as a recommended use-by date or use-within time period.

At block 506, an interrogation signal is received via the antenna of the RFID tag. For example, RFID tag 102(1) may receive an interrogation signal 112 via antenna 106. At block 508, responsive to receipt of the interrogation signal, a parameter derived from a value of the timer is sent via the antenna of the RFID tag. For example, based on an energization by or an inquiry of interrogation signal 112, a parameter derived from a value of timer 330 may be sent (e.g., modulated RF backscatter that is returned, encoded electromagnetic radiation that is reflected, or transmitted) via antenna 106 of RFID tag 102(1). For instance, a remaining time for safe consumption of a perishable product (e.g., a result of subtracting a value of timer 330 from a stored or received perishable period) or a "safe/unsafe" notification may be sent as at least part of a response signal 114.

Figure 6:
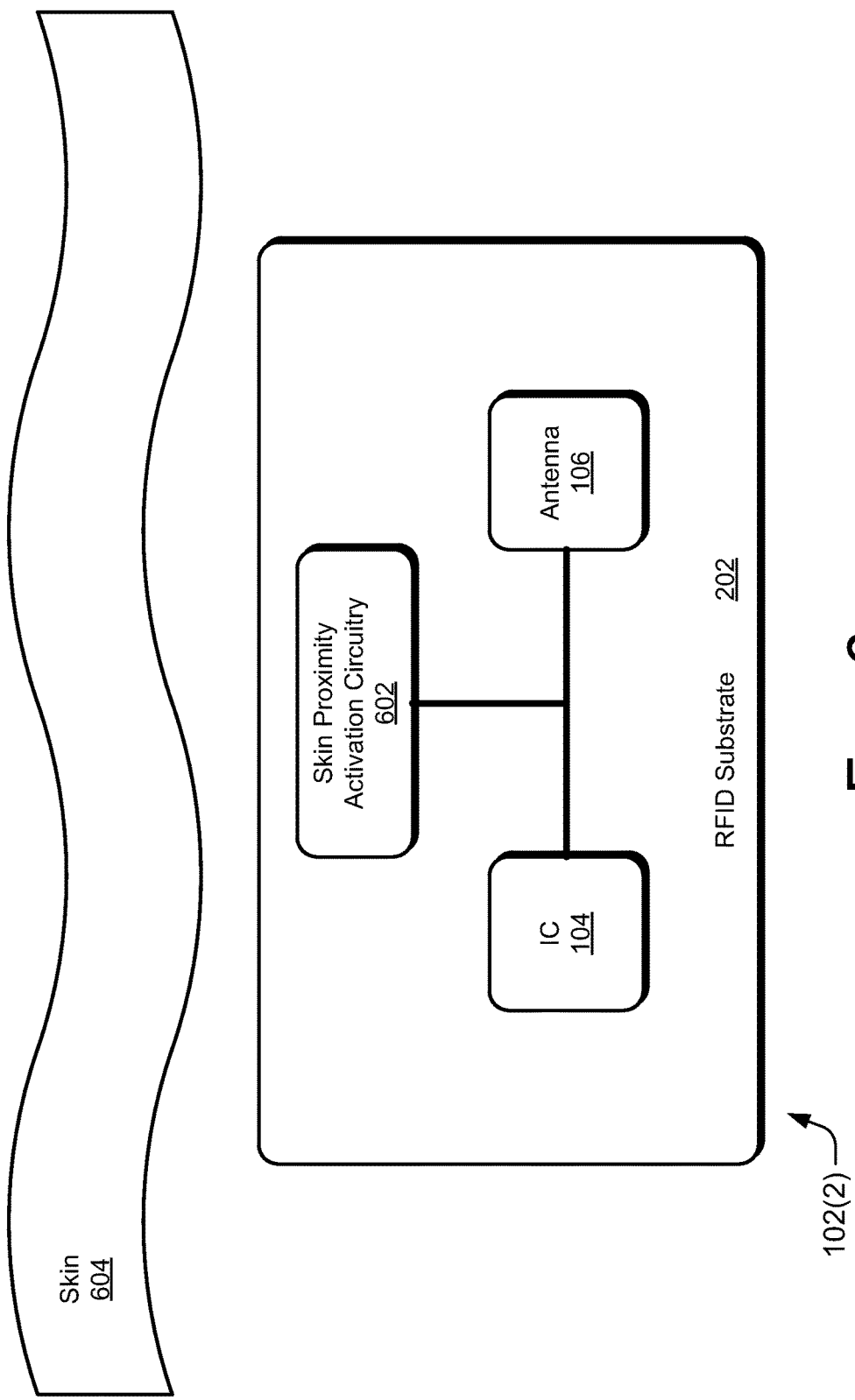
FIG. 6 illustrates an example RFID tag for implementations of person-centric RFID tag activation in accordance with one or more embodiments.
Figures 2, 6:
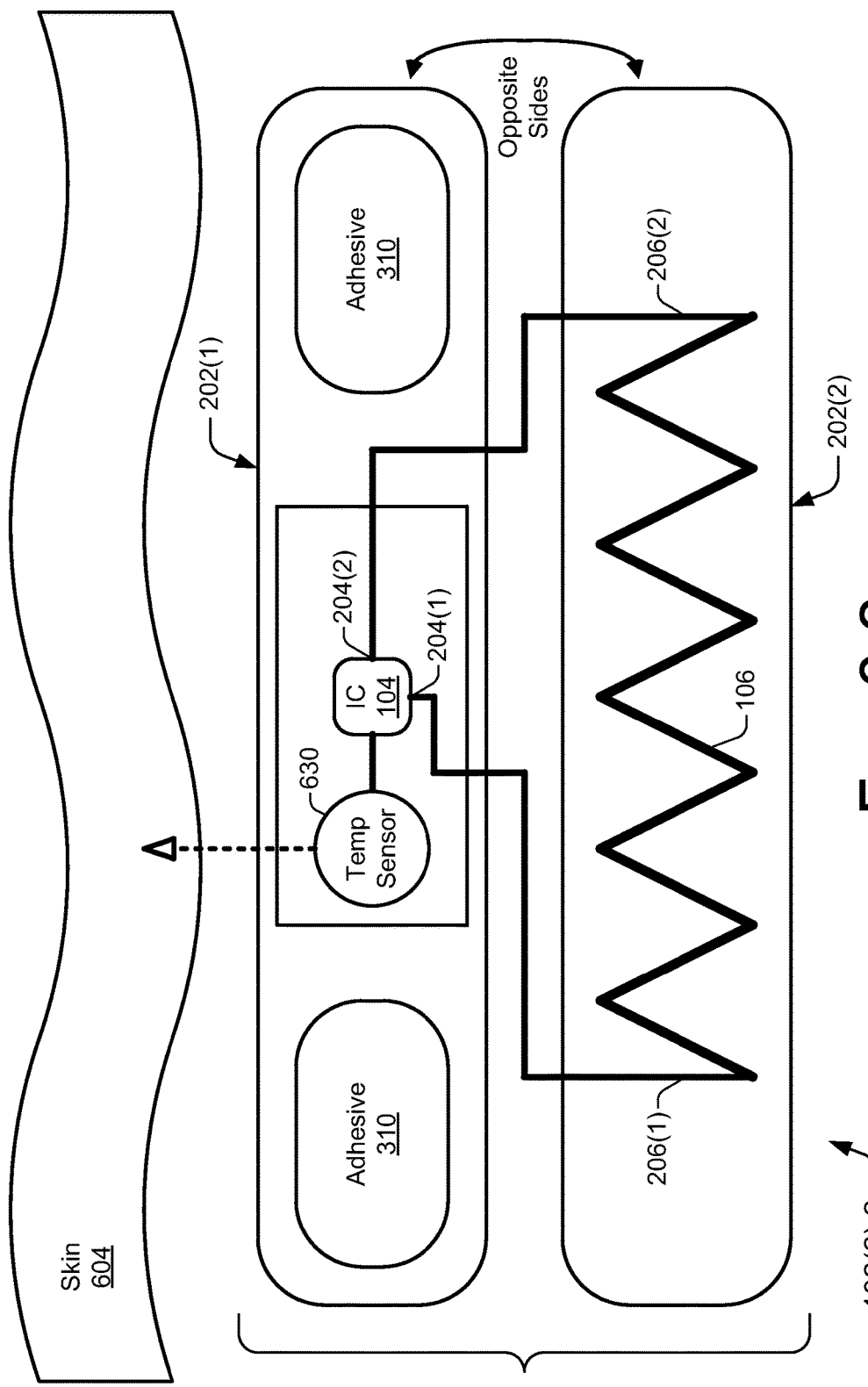

FIG. 6 illustrates an example RFID tag 102(2) for implementations of person-centric RFID tag activation in accordance with one or more embodiments. As illustrated in logical or block diagram form, example RFID tag 102(2) includes an RFID substrate 202, an IC 104, an antenna 106, and skin proximity activation circuitry 602. IC 104 is coupled to antenna 106 or skin proximity activation circuitry 602; antenna 106 is coupled to IC 104 or skin proximity activation circuitry 602; and skin proximity activation circuitry 602 is coupled to IC 104 or antenna 106.

For example embodiments, activation of RFID tag 102(2) is at least partially dependent on a proximity to skin 604 (e.g., human epidermis). RFID tag 102(2) is in an inactive state if RFID tag 102(2) is not proximate to skin 604, but RFID tag 102(2) is in an active state if RFID tag 102(2) is proximate to skin 604. Skin proximity activation circuitry 602, based at least partially on a determination of proximity of RFID tag 102(2) to skin 604, places RFID tag 102(2) in, or causes RFID tag 102(2) to be in, an active state or an inactive state. As discussed further herein below, an RFID tag 102(2) that is in an active state may be in an operationally active state or in a communicatively active state.

An RFID tag 102(2) may be proximate to skin 604, for example, if RFID tag 102(2) is in physical contact with skin 604, if RFID tag 102(2) is touching skin 604, if RFID tag 102(2) is capable of using skin 604 to complete a circuit (e.g., if skin proximity activation circuitry 602 is completed by passing a signal thru skin 604), if RFID tag 102(2) is capable of sensing a person's temperature through skin 604, if RFID tag 102(2) senses a temperature that is within a human-appropriate body temperature range, or some combination thereof. Example implementations in which a skin proximity determination is based at least partially on using skin 604 to complete a circuit of skin proximity activation circuitry 602 are described herein below with particular reference to FIG. 6-1. Example implementations in which a skin proximity determination is based at least partially on sensing a particular temperature (e.g., through skin 604) as performed by skin proximity activation circuitry 602 are described herein below with particular reference to FIG. 6-2. Example implementations that combine skin contact detection with skin temperature detection to determine skin proximity are described herein below with particular reference to FIG. 6-3.

If RFID tag 102(2) is in an operationally active state, RFID tag 102(2) is configured to be capable of receiving, processing, or responding to an interrogation signal or configured to be able to determine if a response to an interrogation signal is to be sent. Example implementations of an RFID tag 102(2) that may be placed in an operationally active state or in an operationally inactive state (e.g., based on skin proximity as detectable by physical contact) are described herein below with particular reference to FIG. 6-1. If RFID tag 102(2) is in a communicatively active state, RFID tag 102(2) is configured to send a response to an interrogation signal. Example implementations of an RFID tag 102(2) that may be placed in a communicatively active state or in a communicatively inactive state (e.g., based on skin proximity as detectable by sensed temperature) are described herein below with particular reference to FIG. 6-2. With regard to FIG. 6-3, skin proximity activation circuitry 602 may place an RFID tag 102(2) (i) into an operationally active state from an operationally inactive state or (ii), while in an operationally active state, into a communicatively active state from a communicatively inactive state.

For one or more example embodiments, antenna 106 is configured to receive an interrogation signal (e.g., an interrogation signal 112). IC 104 is coupled to antenna 106. IC 104 is configured to process and to respond to the interrogation signal if RFID tag 102(2) is in an active state, and IC 104 is configured to not respond to the interrogation signal if RFID tag 102(2) is in an inactive state. Skin proximity activation circuitry 602 is configured to establish the active state if RFID tag 102(2) is proximate to skin 604 or to establish the inactive state if RFID tag 102(2) is not proximate to skin. Example implementations of skin proximity activation circuitry 602 are described below with particular reference to FIGS. 6-1, 6-2, and 6-3.

FIG. 6-1 depicts additional example RFID tag implementations for person-centric activation of RFID tags in accordance with one or more embodiments. As illustrated, RFID tag 102(2)-1 is a schematic diagram of an example RFID tag that is depicted as a medical implement. Specifically, RFID tag 102(2)-1 is shown as a bandage with centralized protective padding, which may include topical medicine, at least one sensor, and so forth. However, RFID tag 102(2)-1 (or RFID tag 102(2)-2 and 102(2)-3 of FIGS. 6-2 and 6-3, respectively) may be realized as another type of medical implement or as another object that is designed or intended to be attached to skin, such as an athletic performance monitoring object.

For example embodiments, RFID tag 102(2)-1 includes an RFID substrate 202 (e.g., also of FIG. 2) having a first RFID substrate side 202(1) and a second RFID substrate side 202(2). Opposite sides of an RFID substrate 202 are shown as first RFID substrate side 202(1) and second RFID substrate side 20(2). Certain components are shown on respective RFID substrate sides to avoid visually obscuring relevant components or interrelationships of the components. Although certain components are shown with respect to a particular substrate side, one or more of the components may be on a same side, may be distributed across the two sides differently than is depicted, may be implemented fully or partially within the substrate, some combination thereof, and so forth.

Second RFID substrate side 202(2) includes an antenna 106 having a first antenna end 206(1) and a second antenna end 206(2). First RFID substrate side 202(1) includes an IC 104 and at least one skin contact point 610 that is part of skin proximity activation circuitry 602 (e.g., of FIG. 6), such as a first skin contact point 610(1) and a second skin contact point 610(2). IC 104 includes a first antenna terminal 204(1) and a second antenna terminal 204(2).

In example operative embodiments, first skin contact point 610(1) is coupled to first antenna end 206(1). Second antenna end 206(2) is coupled to first antenna terminal 204(1) of IC 104. Second antenna terminal 204(2) of IC 104 is coupled to second skin contact point 610(2). Second skin contact point 610(2) and first skin contact point 610(1) may be coupled to skin 604 if RFID tag 102(2)-1 is positioned against a person.

Skin contact point 610 may comprise, for example, a wire tip, a wire pattern, one or more conductive traces, at least one conductive pad, an adhesive portion or area, or some combination thereof. A skin contact point 610 is adapted to establish an electrical connection or a signal coupling between circuitry of RFID tag 102(2)-1 and skin 604 if a skin contact point 610 is positioned against (e.g., is physically touching or makes contact with) skin 604. If two skin contact points 610, such as a first skin contact point 610(1) and a second skin contact point 610(2), are positioned against skin 604, a skin circuit connection 620 may be created between the two skin contact points 610. A skin circuit connection 620 may be located within skin 604, along a surface of skin 604, some combination thereof, and so forth.

For example implementations, a skin circuit connection 620 enables skin proximity activation circuitry 602 (e.g., of FIG. 6), which includes at least first skin contact point 610(1) and second skin contact point 610(2), to be completed. If skin proximity activation circuitry 602 is completed via first and second skin contact points 610(1) and 610(2) along with skin circuit connection 620, an antenna loop is completed for antenna 106 and for first antenna terminal 204(1) and second antenna terminal 204(2) of IC 104. If the circuitry of RFID tag 102(2)-1 is completed, RFID tag 102(2)-1 is operationally active and configured to receive, process, or respond to an interrogation signal 112 (e.g., by sending a response signal 114).

To facilitate creating a skin circuit connection 620 that completes a circuit of RFID tag 102(2)-1, a resistance level of a length or area or volume (along with any potential galvanic response) of skin 604 that is to extend between first skin contact point 610(1) and second skin contact point 610(2) may be considered. An expected (e.g. predicted, probable, or calculated) resistance value range for a skin circuit connection 620 of skin 604 may be, by way of example only, approximately 300 Ohms to 210 K Ohms, with a likely range of 3 K to 100 K Ohms. An expected resistance value for skin 604 may vary based on any one or more of a number of factors, such as water retention, body mass, skin dryness in conjunction with likelihood of or level of perspiration, distance between first and second skin contact points 610(1) and 610(2), width or area of first and second skin contact points 610(1) and 610(2), and so forth. For instance, the above-provided example resistance values may be applicable to a skin circuit connection 620 ranging from a few millimeters (mm) in length to 30 centimeters (cm) in length.

FIG. 6-2 depicts additional example RFID tag implementations for person-centric activation of RFID tags in accordance with one or more embodiments. For example embodiments, RFID tag 102(2)-2 includes an RFID substrate 202 having a first RFID substrate side 202(1) and a second RFID substrate side 202(2). Second RFID substrate side 202(2) includes an antenna 106 having a first antenna end 206(1) and a second antenna end 206(2). First RFID substrate side 202(1) includes an IC 104, at least one adhesive portion 310, and at least one temperature sensor 630 that is part of skin proximity activation circuitry 602 (e.g., of FIG. 6). IC 104 includes a first antenna terminal 204(1) and a second antenna terminal 204(2), and IC 104 may also include at least one terminal for interfacing with a separate sensor (e.g., temperature sensor 630). As shown, first RFID substrate side 202(1) includes two adhesive portions 310, but more or fewer may be included on either or both of first and second RFID substrate sides 202(1) and 202(2).

In example operative embodiments, first antenna terminal 204(1) of IC 104 is coupled to first antenna end 206(1), and second antenna end 206(2) is coupled to second antenna terminal 204(2) of IC 104. As shown, temperature sensor 630 is coupled to IC 104. Alternatively, temperature sensor 630 may be integrated with IC 104. Also, temperature sensor 630 may be disposed at a location different from that which is illustrated. In operation, temperature sensor 630 is adapted to sense or detect a skin temperature of a person via physical contact, an infrared (IR) mechanism, some combination thereof, and so forth. Temperature sensor 630 is configured to provide a temperature value representative of the skin temperature, and IC 104 is configured to obtain the temperature value representative of the skin temperature from temperature sensor 630.

A skin temperature may be representative of an actual surface temperature of skin 604, a body temperature of a person that is measured at or through skin 604, some combination thereof, and so forth. IC 104 may be configured to adjust a detected skin temperature obtained from temperature sensor 630 to account for a location on skin 604 at which temperature sensor 630 is sensing, to account for a mechanism used to sense a skin temperature, to account for a raw or proprietary value provided by temperature sensor 630, some combination thereof, and so forth. IC 104 may be configured to adjust a skin temperature, for example, to convert the skin temperature (i) to a standard body temperature value for comparison purposes or (ii) prior to sending the skin temperature to an RFID reader 110. Alternatively, IC 104 may be configured to compare a raw skin temperature value to one or more thresholds or to send a raw skin temperature value that an RFID reader 110 is programmed to adjust or otherwise utilize.

For example embodiments, skin proximity activation circuitry 602 (not explicitly identified in FIG. 6-2) for RFID tag 102(2)-2 may include temperature sensor 630 and at least part of IC 104. A state of RFID tag 102(2)-2, such as active or inactive, may be established based at least partly on a proximity to skin 604 that is determined responsive to a sensed temperature. For example, if a sensed temperature is above a lower temperature threshold or below an upper temperature threshold or within a specified range of temperatures, RFID tag 102(2)-2 may be placed in an active state.

More specifically, a state of RFID tag 102(2)-2 may comprise a communicatively active state or a communicatively inactive state, depending on a sense temperature. If a sensed temperature is within a person-appropriate temperature range, RFID tag 102(2)-2 may be placed in a communicatively active state in which a received and processed interrogation signal is responded to by sending a response signal. On the other hand if a sensed temperature is not within a person-appropriate temperature range, RFID tag 102(2)-2 may be placed in a communicatively inactive state in which an interrogation signal, even if received and processed, is not responded to by sending a response signal.

A person-appropriate range of temperatures may comprise a range of temperatures or an upper and a lower threshold temperature that is typical of a living person that is healthy or that is unhealthy, depending on context or usage scenario. A full person-appropriate range may extend between, for example, approximately 33.2° C. (91.8° F.) and 41.5° C. (106.7° F.). Other approximate person-appropriate ranges may include, for example: [1] a hypothermia range: below <33.2° C. (91.8° F.); [2] a normal range: 33.2° C. (91.8° F.)-38.2° C. (100.8° F.); [3] a fever range: 38.3° C. (100.9° F.)-41.5° C. (106.7° F.); or [4] some combination thereof. An upper temperature threshold or a lower temperature threshold may be selected from any of these ranges. Additionally, other temperature ranges or temperature thresholds may alternatively be implemented.

For a communicatively inactive state of RFID tag 102 (2)-2, IC 104 may be operationally active, but IC 104 is configured to not respond to an interrogation signal 112. On the other hand, for a communicatively active state of RFID tag 102(2)-2, IC 104 is operationally active, and IC 104 is configured to respond to an interrogation signal 112 with a communication. A communication response to an interrogation signal 112 may include sending a response signal 114. A response signal 114 may include an indication of a sensed temperature value, an indication of a time value (e.g., of an on-board timer indicative of how long a bandage or medicine thereof has been applied), an indication of another sensor value, a parameter derived from a sensed value or a time value, an identification indication (e.g., a name or a patient number or code), some combination thereof, and so forth.

FIG. 6-3 depicts additional example RFID tag implementations for person-centric activation of RFID tags in accordance with one or more embodiments. RFID tag 102(2)-3 combines certain aspects of RFID tag 102(2)-1 (e.g., of FIG. 6-1) and RFID tag 102(2)-2 (e.g., of FIG. 6-2). As illustrated, RFID tag 102(2)-3 includes an RFID substrate 202 (e.g., also of FIG. 2) having a first RFID substrate side 202(1) and a second RFID substrate side 202(2).

Second RFID substrate side 202(2) includes an antenna 106 having a first antenna end 206(1) and a second antenna end 206(2). First RFID substrate side 202(1) includes an IC 104; at least one skin contact point 610 that is part of skin proximity activation circuitry 602 (e.g., of FIG. 6), such as a first skin contact point 610(1) and a second skin contact point 610(2); at least one temperature sensor 630 that is part of skin proximity activation circuitry 602 (e.g., of FIG. 6); and at least one other sensor 640. IC 104 includes a first antenna terminal 204(1) and a second antenna terminal 204(2), and IC 104 may also include at least one terminal for interfacing with a separate sensor (e.g., temperature sensor 630 or other sensor 640).

Although depicted as being separate from IC 104 and temperature sensor 630, other sensor 640 may be integrated with either or both. Although shown at particular locations, temperature sensor 630 or other sensor 640 may be located at a different location, such as a centralized padding area, an adhesive area (e.g., an adhesive portion 310 of FIG. 6-2), a skin contact area (e.g., a skin contact point 610), a location that overlaps multiple areas, and so forth. Also, temperature sensor 630 or other sensor 640 may be co-located with or formed as part of a skin contact point 610.

Examples of other sensors 640 include a motion sensor (e.g., an accelerometer or a gyroscope), an electrical activity sensor (e.g., hospital EKG sensors), a heart-rate sensor, an ambient temperature sensor, an oximetry sensor, a skin conductance sensor, other medical sensors, or some combination thereof. An indication of a sensor value of another sensor 640, or a parameter derived therefrom, may be analyzed by IC 104 or sent as part of a response signal 114. A parameter that is derived from a sensor value may include an average sensor value, a normalized or compensated sensor value, an adjusted sensor value, a description or categorization of a sensor value (e.g., "out-of-range," "level 3," "yellow," "90-92," "within acceptable range," or a combination thereof), a label of a condition corresponding to a sensor value (e.g., "ok," "danger," "safe," "needs attention," or a combination thereof), some combination thereof, and so forth.

In example operative embodiments, first skin contact point 610(1) is coupled to first antenna end 206(1). Second antenna end 206(2) is coupled to first antenna terminal 204(1) of IC 104. Second antenna terminal 204(2) of IC 104 is coupled to second skin contact point 610(2). Second skin contact point 610(2) and first skin contact point 610(1) may be coupled to skin 604 if RFID tag 102(2)-3 is positioned against a person. With such positioning, a skin circuit connection 620 may be created between first and second skin contact points 610(1) and 610(2). As illustrated, temperature sensor 630 is coupled to IC 104. One or more other sensors 640, if present, may also be coupled to IC 104 as shown.

In example implementations, RFID tag 102(2)-3 implements a two-phase mechanism for skin proximity activation circuitry 602. Initially, RFID tag 102(2)-3 is in an inactive state—an operationally inactive and a communicatively inactive state. IC 104 is neither receiving nor processing interrogation signals 112 that arrive at RFID tag 102(2)-3. However, if a power source such as a battery or a capacitor is on-board, IC 104 may be taking sensor measurements and processing (e.g., analyzing, organizing, or storing) them. In an example first phase, RFID tag 102(2)-3 is positioned against skin 604. Skin circuit connection 620 is created and an operational circuit is completed. RFID tag 102(2)-3 establishes an operationally active state in which an interrogation signal 112 may be received and processed by IC 104. However, IC 104 may remain in a communicatively inactive state based on a skin temperature detected by temperature sensor 630.

For a second phase, establishment of a communicatively active state versus a communicatively inactive state depends on a detected temperature. In response to receiving an interrogation signal 112, IC 104 compares a sensed temperature value to a range of temperature values (e.g., to a lower temperature threshold or to an upper temperature threshold) to determine if the sensed temperature value comports with the range of temperature values (e.g., to determine if the sensed temperature value is above the lower temperature threshold or below the upper temperature threshold). If the sensed temperature value comports with the range of temperature values, RFID tag 102(2)-3 is placed in a communicatively active state in which IC 104 may elect to respond to interrogation signal 112 by sending at least one response signal 114. Otherwise, RFID tag 102(2)-3 may remain in an operationally active state but in a communicatively inactive state and may elect to not respond to interrogation signal 112 with a responsive wireless signal.

FIGS. 7 and 8 illustrate example methods for person-centric RFID tag activation in accordance with one or more embodiments. The order in which the methods are described is not intended to be construed as a limitation, and any number or combination of the described method operations can be performed in any order or with any amount of temporal overlap to perform a method, or an alternate method.

For flow diagram 700 of FIG. 7, operations 702-704 may be performed by a person. At block 702, at least one temporary cover is removed to expose a first skin contact point and a second skin contact point of a medical implement comprising an RFID tag that includes an integrated circuit and an antenna. For example, a person may remove at least one temporary cover (e.g., a temporary cover comparable to a temporary adhesive protector 304-1 of FIG. 3-1) to expose a first skin contact point 610(1) and a second skin contact point 610(2) of a medical implement (e.g., a bandage or a sensor patch) comprising an RFID tag 102(2)-1 or 102(2)-3 that includes an IC 104 and an antenna 106.

At block 704, the medical implement is pressed against a person to touch skin at the first skin contact point and at the second skin contact point to complete a circuit including the antenna and to render the integrated circuit capable of responding to an interrogation signal. For example, a person may press the medical implement against a person (e.g., the same or a different person than is performing the pressing) to touch skin 604 at first skin contact point 610(1) and at second skin contact point 610(2) to complete a circuit (e.g., to create a skin circuit connection 620 between first and second skin contact points 610(1) and 610(2) that enables operational activity of a circuit) that includes antenna 106 and to render IC 104 capable of responding to an interrogation signal 112 (e.g., by sending a response signal 114).

For flow diagram 800 of FIG. 8, operations 802-808 may be performed by an RFID tag 102. Methods or operations described herein can be implemented using hardware in conjunction with software, firmware, fixed logic circuitry, a combination thereof, and so forth. Some operations of the example methods may be described in a general context of processor-executable instructions that are stored on processor-accessible (e.g., computer-readable) storage memory that is part of an RFID tag 102 (e.g., that is disposed on an RFID substrate 202 as part of, or separate from, an IC 104).

Although not shown in flow diagram 800, one or more of the operations that are illustrated may further include or another operation may include routing via skin a current signal for at least one of an integrated circuit or an antenna of an RFID tag. For example, a current signal may be routed via a skin circuit connection 620 through skin 604 for at least one of an IC 104 or an antenna 106 for an RFID tag 102(2)-3 implementation of an RFID tag. At block 802, a skin temperature is sensed to detect a temperature value. For example, a temperature sensor 630 of an RFID tag 102(2)-2 or 102(2)-3 may sense skin temperature with respect to skin 604 to detect a temperature value.

At block 804, the detected temperature value is compared to at least one temperature threshold. For example, an IC 104 of RFID tag 102(2)-2 or 102(2)-3 may compare the detected temperature value to an upper temperature threshold or to a lower temperature threshold. For instance, IC 104 may determine if the detected temperature value is above the lower temperature threshold and below the upper temperature threshold. At block 806, an RFID interrogation signal is received. For example, IC 104 may receive an interrogation signal 112 via an antenna 106 of RFID tag 102(2)-2 or 102(2)-3.

At block 808, it is determined whether to respond to the RFID interrogation signal based on said comparing. For example, IC 104 may determine if RFID tag 102(2)-2 or 102(2)-3 is to respond to interrogation signal 112 based at least partially on a comparison including the detected temperature value and at least one temperature threshold. For instance, IC 104 may (i) elect not to send a response signal 114 if the detected temperature value is below a lower temperature threshold and (ii) elect to wirelessly send response signal 114 if the detected temperature value is above the lower temperature threshold. Additionally or alternatively, IC 104 may (i) elect not to send response signal 114 if the detected temperature value is above the upper temperature threshold and (ii) elect to wirelessly send response signal 114 if the detected temperature value is below the upper temperature threshold.

Although embodiments of on-demand activation of RFID tags and person-centric activation of RFID tags have been described in language specific to features and/or methods, the subject of the appended claims is not necessarily limited to the specific features or methods described. Rather, the specific features and methods are disclosed as example implementations of on-demand RFID tag activation and person-centric RFID tag activation, and other equivalent features and methods are intended to be within the scope of the appended claims. Further, various different embodiments are described and it is to be appreciated that each described embodiment can be implemented independently or in connection with one or more other described embodiments.

The invention claimed is:

1. A radio frequency identification (RFID) tag, comprising:
    an antenna configured to receive an interrogation signal;
    an integrated circuit coupled to the antenna, the integrated circuit configured to respond to the interrogation signal if the RFID tag is enabled, and configured to not respond to the interrogation signal if the RFID tag is not enabled; and
    skin proximity activation circuitry that is configured to enable the RFID tag responsive to the RFID tag being placed into contact with skin, or to disable the RFID tag responsive to the RFID tag not being in contact with the skin, the skin proximity activation circuitry configured to have an open circuit when the RFID tag is not in contact with the skin, the skin acting to complete the open circuit when the RFID tag is in contact with the skin.

2. The RFID tag as recited in claim 1, wherein the RFID tag comprises at least a portion of a medical implement.

3. The RFID tag as recited in claim 2, wherein the medical implement comprises a bandage including adhesive that is adapted to secure the bandage to the skin.

4. The RFID tag as recited in claim 2, wherein the medical implement comprises a sensor and includes adhesive that is adapted to secure the sensor to the skin.

5. The RFID tag as recited claim 1, wherein the RFID tag further comprises a first skin contact point and a second skin contact point, the first skin contact point comprising a first adhesive skin pad, and the second skin contact point comprising a second adhesive skin pad.

6. The RFID tag as recited in claim 1, wherein:
    the antenna includes a first antenna end and a second antenna end;
    the integrated circuit includes a first antenna terminal and a second antenna terminal; and
    a first skin contact point is coupled to the first antenna end, the second antenna end is coupled to the first antenna terminal of the integrated circuit, and the second antenna terminal of the integrated circuit is coupled to a second skin contact point.

7. The RFID tag as recited in claim 1, wherein the RFID tag further comprises a temperature sensor that is adapted to produce a temperature value responsive to a skin temperature.

8. The RFID tag as recited in claim 7, wherein the skin proximity activation circuitry is configured to establish whether the RFID tag is enabled or the RFID tag is disabled based on the temperature value.

9. The RFID tag as recited in claim 8, wherein the skin proximity activation circuitry is configured to establish the RFID tag is enabled if the temperature value is above a lower temperature threshold or to establish the RFID tag is disabled if the temperature value is below the lower temperature threshold.

10. A radio frequency identification (RFID) tag, comprising:
    a first skin contact point;
    a second skin contact point;
    an integrated circuit including a first antenna terminal and a second antenna terminal, the second antenna terminal of the integrated circuit coupled to the second skin contact point, the integrated circuit configured to be enabled when the first contact point and the second contact point contact a surface of skin and configured to be disabled when the first contact point or the second contact point do not contact the surface of skin, the integrated circuit configured to have an open circuit when the RFID tag is not in contact with the surface of skin, the surface of skin acting to complete the open circuit when the RFID tag is in contact with the surface of skin; and
    an antenna including a first antenna end and a second antenna end, the first antenna end coupled to the first skin contact point and the second antenna end coupled to the first antenna terminal of the integrated circuit.

11. The RFID tag as recited in claim 10, wherein the integrated circuit is configured to detect an interrogation signal that is received via the antenna if the skin proximity activation circuitry is completed by the skin.

12. The RFID tag as recited in claim 10, wherein:
    the RFID tag further comprises a temperature sensor that is adapted to detect a skin temperature; and
    the integrated circuit is configured to respond to a received interrogation signal based on the detected skin temperature.

13. The RFID tag as recited in claim 12, wherein:
    the integrated circuit is configured to send a response signal via the antenna if the detected skin temperature comports with a temperature range.

14. A method, comprising:
    receiving an interrogation signal with an antenna of a radio frequency identification (RFID) tag;
    responding to the interrogation signal based on an enablement of the RFID tag, said responding with an integrated circuit that is coupled to the antenna if the RFID tag is enabled, and not responding to the interrogation signal if the RFID tag is disabled; and
    establishing enablement of the RFID tag if the RFID tag is in contact with skin, or disablement of the RFID tag if the RFID tag is not in contact with the skin by having an open circuit of the RFID tag when the RFID tag is not in contact with the skin, the skin acting to complete the open circuit when the RFID tag is in contact with the skin.

15. The method as recited in claim 14, wherein the RFID tag comprises at least a portion of a medical implement.

16. The method as recited in claim 15, wherein the medical implement comprises a bandage including adhesive that is adapted to secure the bandage to the skin.

17. The method as recited in claim 15, wherein the medical implement comprises a sensor and includes adhesive that is adapted to secure the sensor to the skin.

18. The method as recited claim 14, wherein the RFID tag comprises a first skin contact point and a second skin contact point, the first skin contact point comprising a first adhesive skin pad, and the second skin contact point comprising a second adhesive skin pad.

19. The method as recited in claim 14, wherein the RFID tag further comprises a temperature sensor, the temperature sensor configured to produce a temperature value responsive to a skin temperature.

20. The RFID tag as recited in claim 9, wherein the skin proximity activation circuitry is further configured to establish the RFID tag is enabled if the temperature value is below an upper temperature threshold or to establish the RFID tag is disabled if the temperature value is above the upper temperature threshold.

* * * * *